United States Patent [19]

Ryerson

[11] 4,240,799
[45] Dec. 23, 1980

[54] SENSING THE PRESENCE OF OZONE

[75] Inventor: John D. Ryerson, Holland Patent, N.Y.

[73] Assignee: Energy for Independence, Inc., Holland Patent, N.Y.

[21] Appl. No.: 63,210

[22] Filed: Aug. 3, 1979

[51] Int. Cl.³ .................. G01N 27/04; H01C 7/00
[52] U.S. Cl. .................. 23/232 E; 73/27 R; 324/71 SN; 338/34; 422/90; 422/98
[58] Field of Search ............... 422/90, 97, 98; 23/232 E; 338/34; 324/71 SN; 73/27

[56] References Cited

U.S. PATENT DOCUMENTS

| | | | |
|---|---|---|---|
| 3,611,243 | 10/1971 | Hardtl | 338/34 |
| 3,625,756 | 12/1971 | Taguchi | 338/34 |
| 3,695,848 | 10/1972 | Taguchi | 324/71 SN |
| 3,699,803 | 10/1972 | Sumi et al. | 324/71 SN |
| 3,778,229 | 12/1973 | Webster et al. | 422/98 |
| 4,001,756 | 1/1977 | Heijne | 338/34 |
| 4,039,941 | 8/1977 | Morrison | 422/98 |
| 4,045,178 | 8/1977 | Okiraka | 422/98 |

Primary Examiner—R. E. Serwin
Attorney, Agent, or Firm—Bruns & Jenney

[57] ABSTRACT

A means for detecting and/or measuring the presence of ozone in an atmosphere such as air. A solid state sensor that is capable of changing its conductivity in the presence of ozone is located within a housing along with an ultraviolet lamp and a stream of the sampled atmosphere caused to pass over the sensor. After exposure to ozone in the atmosphere, the sensor is restored to its initial or start of sensing state by flooding it with ultraviolet radiation produced by the lamp.

16 Claims, 3 Drawing Figures

U.S. Patent  Dec. 23, 1980  4,240,799
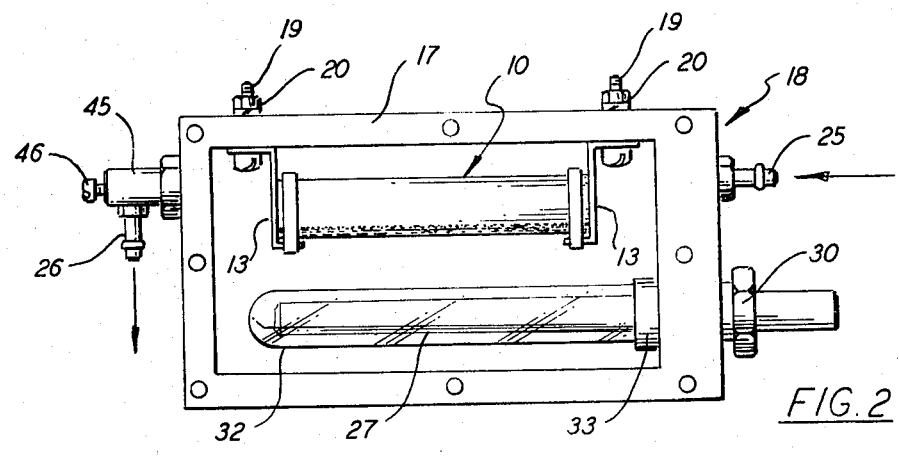
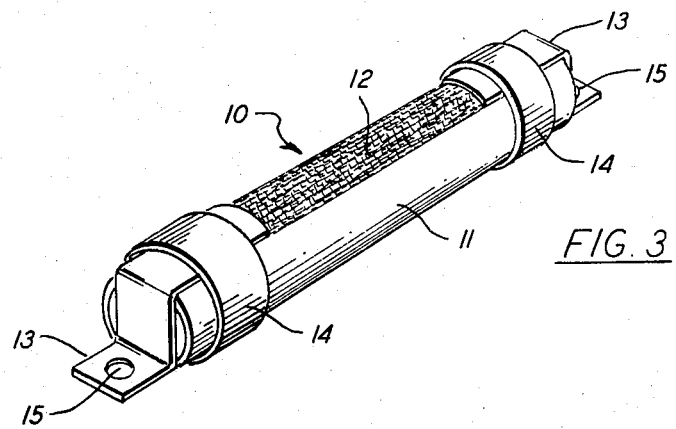
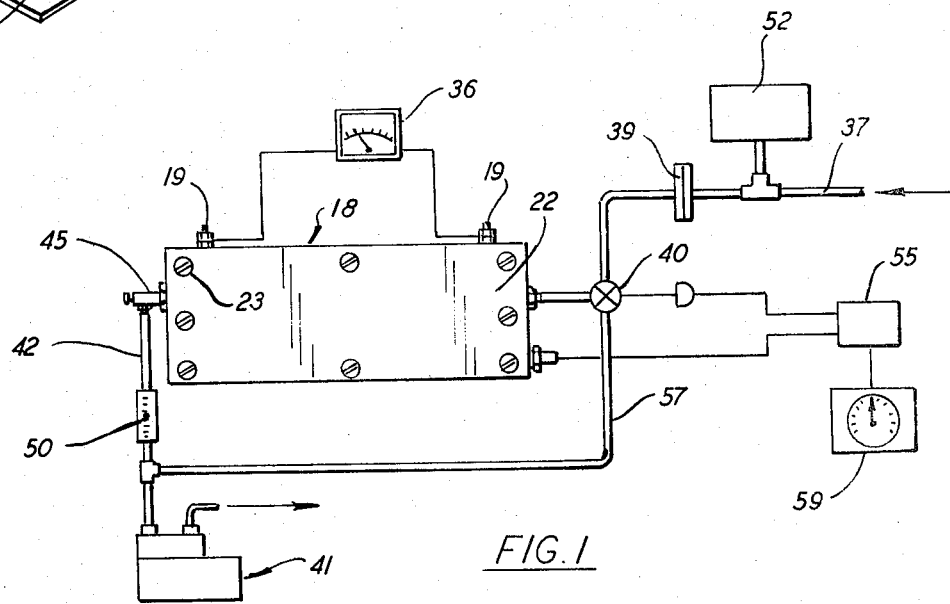

SENSING THE PRESENCE OF OZONE

BACKGROUND OF THE INVENTION

This invention relates to means for detecting the presence of ozone in an atmosphere and, in particular, to an ozone detecting device that utilizes a solid state sensing element in conjunction with an ultraviolet lamp for restoring the sensor to its initial sensing condition after it has been exposed to ozone.

It is well known that the presence of small amounts of ozone in air can be harmful to humans and have an adverse effect on all living organisms and their environment. One area of immediate concern involves high flying aircraft that are capable of passing through the earth ozone layer. Since most aircraft draw at least some of the cabin air from the surrounding atmosphere, it is quite possible to expose those on board to potentially harmful levels of ozone for relatively long periods of time. Because of the nature of ozone, its presence cannot normally be detected without resorting to use of specialized instruments which heretofore were wholly unsuited for use in this type of application.

Three well-known methods of detecting the presence of ozone in air include wet chemistry processes, ultraviolet absorption techniques and chemilum inescents. These processes all work very well but require complex equipment to implement which is difficult to set up and maintain. Typically, these processes are better suited for use in a laboratory than in most industrial applications. Another disadvantage associated with many of the prior art detecting processes that might further limit their applicability involves a slow response time upon exposure to ozone along with an equally slow recovery period.

SUMMARY OF THE INVENTION

It is therefore an object of the present invention to improve means for detecting the presence of ozone in an atmosphere and, in particular, in air.

A further object of the present invention is to provide detecting equipment that is able to rapidly and repeatably detect the presence of small amounts of ozone in an atmosphere.

A still further object of the present invention is to improve the means by which a solid state ozone detector can be restored to its initial sensing state after it has been exposed to ozone.

Another object of the present invention is to provide a rugged, easy to operate, ozone detecting device that employs a solid state sensor that is capable of detecting and measuring the amount of ozone present in an atmosphere.

Yet another object of the present invention is to provide a fully automatic ozone detecting system that is suitable for use in high flying aircraft.

These and other objects of the present invention are attained by an ozone detecting system having a solid state sensor that is capable of changing its conductivity in the presence of ozone, means to expose the sensor to an atmosphere, and radiant means focused upon the sensor for restoring the sensor to its initial pre-exposure state after each detecting cycle.

BRIEF DESCRIPTION OF THE DRAWINGS

For a better understanding of these and other objects of the present invention reference is had to the following detailed description of the invention that is to be read in conjunction with the accompanying drawings, wherein:

FIG. 1 is a schematic diagram of a detecting system for sensing the presence of ozone in an atmosphere which embodies the teachings of the present invention.

FIG. 2 is an enlarged side elevation of the detector housing employed in the system of FIG. 1 with its side cover being broken away to show the sensor and the purge lamp contained therein, and FIG. 3 is an enlarged perspective view of a solid state sensor employed in the practice of the present invention.

DESCRIPTION OF THE INVENTION

Referring initially to FIG. 3, there is shown a solid state sensor, generally referenced 10, that is uniquely suited for detecting relatively small amounts of ozone in an atmosphere such as air. A sensor of this nature is described in greater detail in pending U.S. application Ser. No. 888,228 which was filed Mar. 20, 1978. It has been found that a low valence form of a multi-valence metal oxide, such as stannous oxide, has the ability to rapidly change its resistance or conductivity when it is exposed to ozone in air at ambient temperatures and pressures. When placed in a porous thick film configuration, the metal oxide exhibits a relatively low impedance, somewhere in the 50K to 100K ohms range, and thus is ideally well suited for direct use in all forms of electronic circuitry. The sensor has been found to be stable under normal operating conditions, highly sensitive to ozone and free from thermal noise.

As illustrated in FIG. 3 the present sensor includes a substrate in the form of a hollow quartz rod 11 upon which is supported a semiconductor coating 12. The coating preferably is stannous oxide which is fused to the quartz rod in the form of granular particles to provide a rough textured surface having a uniform thickness of between 200,000 and 250,000 angstroms thick. The coating extends longitudinally along the length of the rod and covers about one-quarter or 90° of the rod circumference. At each end of the sensor a Z-shaped contact 13 is held in electrical contact with the semiconductive coating by means of a clamping band 14. A hole is provided in the contact to enable the sensor to be secured to a support surface in assembly.

With further reference to FIGS. 1 and 2, the sensor 10 is secured to the inner top wall 17 of detector housing 18 using two threaded electrical terminals 19—19. In assembly, the terminals are passed through the sensor contacts and the top wall of the housing to mount the sensor in an inverted position as shown in FIG. 2. The sensor is locked in place using nuts 20—20.

The housing is generally rectangular in shape and is preferably made of aluminum that is coated with an inert material such as Teflon. Access to the housing is provided by a side wall cover Plate 22 that is affixed to the housing using screws 23—23. Although not shown, a Teflon gasket is positioned between the housing and the cover plate to furnish a seal therebetween which renders the housing gas-tight when the cover is bolted in place. An inlet hose connector 25 and an outlet hose connector 26 are fitted into the two opposing end walls of the housing. The connectors permit a stream of air or atmosphere to be passed through the sealed housing.

An ultraviolet lamp 27 is mounted in horizontal alignment within the housing from one of the end walls using an O-ring and gland nut combination 30. The lamp is supported directly beneath the semiconductive coating 12 of the sensor. The lamp is shielded from the atmosphere contained within the housing by means of a glass envelope 32 and a sealing mechanism 33. In assembly, the radiant energy emitted by the lamp is able to completely flood the entire semiconductor region on the sensor with light.

When the sensor is exposed to ozone, a portion of the lower valence oxides are oxidized to the next higher level thereby producing a discernible change in the sensor's conductivity by reduction of the N-type carriers that are available. It normally takes the sensor a relatively long period of time to recover from the adsorption effects of ozone. However, it has been found that recovery can be dramatically speeded up and made controllable by exposing the sensor to ultraviolet radiation after the ozone has been removed from the system. The ultraviolet light emitted by the lamp generates photons with sufficient energy to reduce the high valence oxides to the next lower level thereby rapidly restoring the sensor to its initial electrical conductivity. The energy required to convert stanic oxide back to stannous oxide corresponds with the photon energy of ultraviolet light that is at a wavelength somewhere between 300 and 500 NM. The use of a glass or quartz substrate in the sensor structure has also been found to be desirous in that the glass allows the radiant energy to pass therethrough whereupon it is able to reach all exposed areas of the semiconductor.

Turning now to FIG. 1, there is illustrated a system for both detecting and measuring the amount of ozone present in an atmosphere which utilizes the solid state sensor and ultraviolet restoring lamp shown in FIG. 2. The sensor terminals 19—19 are connected to an ohmmeter 36 that is able to detect changes in the sensor's resistance and thus provide an indication of the presence of ozone in the atmosphere contained within the detector housing. A sample of the atmosphere is brought into the system via inlet line 37. Prior to entering the housing, the sample is passed through a filtering mechanism 39 containing a 5 micron screen capable of removing airborne contaminants from the sample which might produce an erroneous sensor reading. Upon leaving the filter the sample passes through an electrically controlled three-way valve 40 and enters the housing via inlet connection 25.

The sample atmosphere is drawn through the housing by means of a suction pump 41 acting through line 42. An adjustable needle valve 45 is operatively connected into the outlet connector 26 and includes an adjusting means 46 by which the rate of flow through the housing can be adjusted. A suitable flow indicator 50 is connected into line 42 to provide a visual indication of the actual flow passing therethrough.

An ozone generator 52 is also connected into the inlet line 37 of the system and is used to calibrate the system so that accurate measurements of the ozone present in a sample may be taken. For purposes of explanation, it will be assumed that the initial start of sensing state of the sensor is 500 ohms. The sensor can be either above or below the desired ohmic value. Should the value be above 500 ohms, it is necessary to turn on the ultraviolet lamp whereupon the resistance of the sensor is lowered photolytically. When the resistance reaches the initial start of detecting value, the lamp is switched off.

Switching on and off of the lamp is accomplished by means of switch means 55. The switch means also controls the activity of three-way valve 40 and causes the incoming flow to be shunted directly to the pump via shunt line 57 when the lamp is in the on condition. This prevents further exposure of the sensor to ozone during the time it is being purged by the radiant energy source.

A sample of air containing a known concentration of ozone is then fed from the generator through the housing. At the precise moment that the generator air is admitted to the housing, a timer 59 is started. When the resistance of the sensor reaches a second higher value, as for example 1000 ohms, the timer is stopped and the flow diverted from the housing. The elapsed time required for the change in ohmic value to occur is noted.

The sensor is then returned to its initial starting resistance using the purge lamp and a second sample at another ozone level is fed into the housing to establish another time rate of change reading. After several known levels of ozone are sampled and the elapsed times established, a calibration curve is plotted for the sensor. Upon exposure to an unknown concentration of ozone, the elapsed time to produce a given change in the sensor's resistance is noted and the actual concentration is determined from the calibration curve. As can be seen, the sensor is thus able to provide a rapid indication of the presence of ozone and also give an extremely accurate reading of the concentration of ozone that is present in a sampled atmosphere.

While this invention has been described with reference to the structure disclosed herein, it is not confined to the details set forth and this application is intended to cover any modifications or changes as may come within the scope of the following claims.

I claim:
1. The method of detecting the presence of ozone in an atmosphere including the steps of
    exposing a solid state sensor that is capable of changing its conductivity in the presence of ozone to an atmosphere,
    detecting the change in conductivity of said sensor upon its exposure to said atmosphere, and
    flooding the sensor with ultraviolet radiation after exposure to said atmosphere to restore it to its initial pre-exposure conductive state whereby the sensor is able to carry out another detecting cycle.
2. The method of claim 1 that further includes the step of metering a controlled flow of atmosphere past the sensor.
3. The method of claim 2 that further includes the step of terminating the flow of atmosphere past the sensor during the period it is being flooded with ultraviolet radiation.
4. The method of claim 2 that further includes the step of filtering the atmosphere prior to exposing the sensor thereto to prevent contaminants from contacting the sensor.
5. The method of claim 1 further including the step of calibrating the response of the sensor by exposing the sensor to accurately controlled quantities of ozone whereby the response of the sensor to known quantities of ozone can be calibrated.
6. Apparatus for detecting the presence of ozone in an atmosphere that includes
    a gas-tight housing,
    flow means for admitting an atmosphere into said housing,
    a solid state sensor that is capable of changing its conductivity in the presence of ozone within the housing whereby the sensor is exposed to said atmosphere, admitted to said housing, and a source of ultraviolet radiation also located within the housing to radiate energy upon said sensor whereby the sensor can be restored to its initial pre-exposure conductive state after it has been exposed to ozone.

7. The apparatus of claim 6 wherein said flow means further includes a control means for metering the flow through said housing at a desired rate.

8. The apparatus of claim 6 further including a detector means electrically connected to the sensor for detecting a change in conductivity of said sensor.

9. The apparatus of claim 7 further including switch means for terminating the flow of atmosphere through the housing during the time that the ultraviolet source is radiating.

10. The apparatus of claim 7 that further includes a filter that is connected to the flow means and which is arranged so that the flow of atmosphere admitted to the housing passes therethrough whereby particulate material is removed from said atmosphere.

11. The apparatus of claim 9 that further includes an ozone generator connected to said flow means that is operable to deliver a desired quantity of ozone into the housing whereby the reaction of said sensor to a known quantity of ozone can be calibrated.

12. The apparatus of claim 11 further including a timing means operatively connected to the switch means for controlling the flow time of said atmosphere and the radiating period of said source.

13. The apparatus of claim 6 wherein said radiation is within a range of between 300 and 500 NM.

14. In a device for detecting the presence of ozone in an atmosphere of the type utilizing a solid state sensor that is capable of changing its conductivity when exposed to ozone in an atmosphere, the improvement comprising
a source of ultraviolet radiation that is arranged to flood the sensor with radiation whereby the sensor is restored to its initial conductivity after it has been exposed to ozone.

15. The improvement of claim 14 wherein said radiation is between 300 and 500 NM.

16. The improvement of claim 14 that further includes a switch means for activating and inactivating said source.

* * * * *